United States Patent [19]

Tani

[11] Patent Number: 5,683,697
[45] Date of Patent: Nov. 4, 1997

[54] PHARMACEUTICAL COMPOSITION FOR TREATING AIDS

[76] Inventor: Michio Tani, Tani Clinic, Akasaka Yu Bld. 6F, 5-4-10, Akasaka, Minato-ku, Tokyo, Japan

[21] Appl. No.: 540,031

[22] Filed: Oct. 6, 1995

Related U.S. Application Data

[63] Continuation of Ser. No. 154,405, Nov. 19, 1993, abandoned.

[51] Int. Cl.$^6$ .................................................. A61K 35/78
[52] U.S. Cl. ........................................ 424/195.1; 514/885
[58] Field of Search ........................... 424/195.1; 514/885

[56] References Cited

U.S. PATENT DOCUMENTS

| | | | |
|---|---|---|---|
| 4,871,540 | 10/1989 | Kojima | 424/195.1 |
| 5,032,580 | 7/1991 | Watanabe | 514/23 |
| 5,055,297 | 10/1991 | Fujimari | 424/195.1 |
| 5,204,101 | 4/1993 | Stubblefield | 424/195.1 |

OTHER PUBLICATIONS

Steinmetz E. F., Codex Vegetabilis, Amsterdam 1957, #704, 584, 314, 316, 905, 403, 803, 12, 525.

Kusumoto, It., Screening Some Indonesian Medicinal Plants for Inhibitory Effects on HIV-1 Protease, Japanese J of Pharmacognosy 46 (2) 1992, pp. 190–193.

*Primary Examiner*—Ralph Gitomer
*Attorney, Agent, or Firm*—Foley & Lardner

[57] ABSTRACT

A pharmaceutical composition for treatment of AIDS comprising (1) herb medicines having anti-inflammatory anti-fever, expectorant or anti-tussive action, (2) herb medicines having nourishment, tonic, gastrointestinal tract function-improving or digestive action, and (3) herb medicines having anti-fungal or anti-viral action.

11 Claims, 3 Drawing Sheets

DIFFERENCES OF CLINICAL EFFECT BETWEEN GROUPS TREATED WITH HERB (A) AND WITHOUT HERB (B)

PHARMACEUTICAL COMPOSITION FOR TREATING AIDS

This application is a continuation of application Ser. No. 08/154,405, filed Nov. 19, 1993 now abandoned.

BACKGROUND OF THE INVENTION

1. Field of the Invention

The present invention provides a pharmaceutical composition for treating acquired immune deficiency syndrome (AIDS).

2. Related Art

Ever since AIDS was first reported in the U.S. in 1981, the number of persons afflicted with this disease has risen rapidly, with recent reports indicating that the number has grown to 300,000 with an additional 1.2 million carriers in the U.S. alone. At present, although the virus has been identified and aggressive efforts are being made to develop effective methods of treatment and prevention of AIDS throughout the world, a suitable means of treatment and prevention has yet to be discovered as of 1993. Moreover, the spread of this disease is much faster than what was originally expected, with current estimates indicating that the number of persons suffering from this disease will reach more than 40 million on a global scale at the end of this century. Thus, development of a means of prevention and discovery of an effective treatment method are being hoped for as quickly as possible. Although the development of a vaccine would be the most desirable, there are currently no vaccines being developed considered to be effective, and the time schedule for their completion remains undetermined. Moreover, the number of therapeutic drugs, such as AZT (amidothymidine) and DDT, are extremely few, the completion of an effective therapeutic drug appears to be a long way off, and there are serious adverse side effects, including bone marrow function disorders and liver function disorders, that make adequate continuous therapy essentially impossible. DDI (dideoxyinosine) and DDC (dideoxycytidine) and other drugs that have recently come into widespread use have effects similar to those of AZT, and there are have been no reports of these drugs resulting in successful treatment anywhere in the world thus far. Moreover, since patients are dying within only several years after onset of the disease and the mortality rate is 100%, AIDS is considered to be one of the most threatening diseases to face mankind in recorded history.

The disease mechanism of AIDS first begins with invasion of viruses to $CD_4$ lymphocytes, which serve as the basis of the immune system, the basic defense mechanism of the human body. These lymphocytes are successively destroyed resulting in acquired immunodeficiency. Ultimately, the disease invariably results in death caused by serious infection, malignant tumors such as Kaposi's sarcoma, and direct damage of the nervous system by the virus. The stages from infection to death can be broadly divided into the following three stages.

(1) An asymptomatic stage extending from the time after infection to the manifestation of some form of subjective or objective symptoms, namely the HIV carrier stage;

(2) A stage in which various symptoms are presented including infections resulting from lowered immunity, namely the ARC (AIDS related complex) stage; and, (3) The final stage that leads to death after passing through a stage involving various serious symptoms occurring based on the reduction of $CD_4$ lymphocytes, such as Karini's pneumonia and including the characteristic opportunistic infections associated with AIDS.

Therefore, in addition to early treatment of the opportunistic infections, treatment currently being considered attempts to take steps regress from stage (3) to stage (2), from stage (2) to stage (1) and if possible, to maintain the patient at stage (1) or (2) for an extended period of time once onset of the disease has begun.

SUMMARY OF THE INVENTION

The object of the present invention is to provide a pharmaceutical composition for the treatment of AIDS that is effective against AIDS and has hardly any adverse side effects.

In order to achieve the objective described above, the present invention provides a pharmaceutical composition comprising herb medicines of the group:

(1) at least a herb medicine having an anti-inflammatory, anti-fever, expectorant or anti-tussive action, selected from the group consisting of *Melia azedarach* L., *Angepica dahurica* B & H., *Dendrobium hancockii* R., *Impatiens balsamina* L., *Citrus medica* L., *Loranthus parasiticus* Merr., seeds of *Celosia argentea* L., roots of *Cynanchum glaucescens* (Decne) Hand. Mazz., and *Glehnia littoralis* Fr;

(2) at least a herb medicine having a nourishment, tonic, good for gastrointestinal tract, or digestive action, selected from the group consisting of *Prunus amygdalus* Batsch., *Dioscorea batatas* Decne., *Dendrobium hancockii* R., *Loranthus parasiticus* Merr., *Paullinia cupana* Kunth, *Acer saccarum* Marsh., *Citrus medica* L., and *Glycyrrhiza glabra* L.; and (3) at least a herb medicine having an anti-fungal or anti-viral action, selected from the group consisting of *Glehnia littoralis* Fr., *Angepica dahurica* B & H, *Loranthus parasiticus* Merr., *Impatiens balsamina* L., and *Gloiopeltis tenax* T.A.

DETAILED DESCRIPTION OF THE INVENTION

Figure 1:
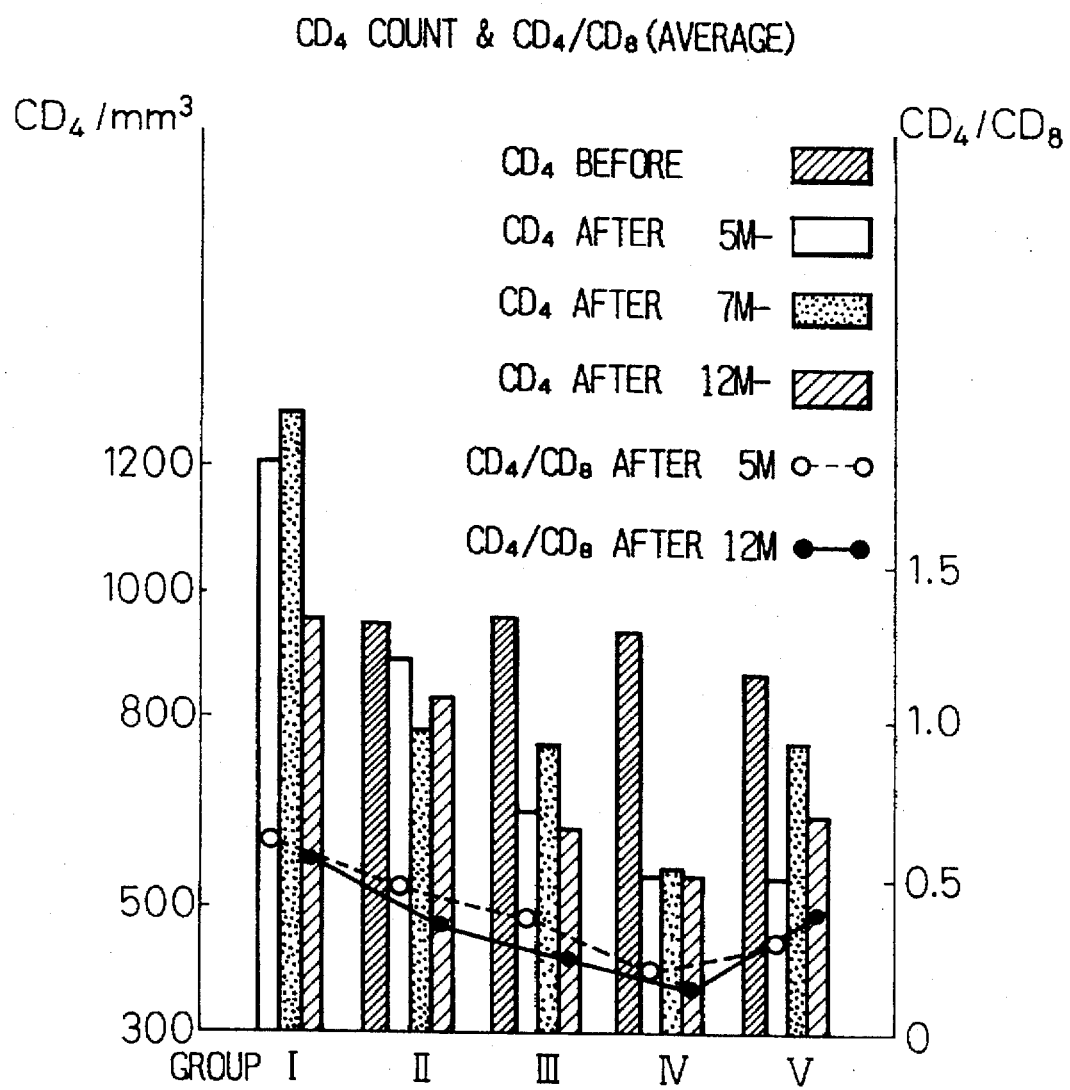
FIG. 1 is a graph showing a $CD_4$ cell count of patient groups treated with the present composition or other medicines.

The inventors of the present invention first considered the concepts described below. (1) Substances should be used for the raw material that are found in nature, and particularly in plants (herb medicine), either have no or little toxicity, and are essentially free of adverse side effects on the human body. In addition, it is preferable that the substances also have tonic action if possible. (2) Substances should be used that inhibit the activity of HIV virus as much as possible. In addition, herb medicines having anti-biotic action as well as anti-viral action against as broad a spectrum of microbes as possible should be used to prevent the occurrence of infections in AIDS patients as much as possible. (3) Herb medicines should be used that have immunity enhancing action in order to supplement the weakened immunity of AIDS patients. In addition, substances should be used that have the function of an internal cytokine inducer such as interferon that acts on immune activity. (4) Herb medicines should be used that has action which increase the production of $CD_4$ lymphocytes selectively destroyed by the AIDS virus, namely an herb medicine that has the action of increasing the $CD_4/CD_8$ ratio. (5) AIDS patients typically suffer from decreased gastrointestinal function, and particularly chronic diarrhea, absorption of nutrients is remarkably impaired, and as a result, tend to become malnourished resulting in promotion of progress of the disease. It is therefore desirable that herb medicines be used that also have action that maintains the stomach in a healthy state, are good for the gastrointestinal tract and prevent diarrhea. In addition, herb medicines should be used that are able to accommodate other symptoms that are manifested at a high rate, including febricula, lymphoma, bronchitis and pneumonia.

However, in the case of treatment using various herb medicines, wherein each herb medicine contains, numerous types of active ingredients, new combinations must be created in which synergistic effects and conflicting effects of the respective effective actions of the herb medicines as well as new effects are demonstrated resulting from combining several types of herb medicines and blending in different amounts. However, although practitioners of oriental medicine (herbal medicine) in China, Japan and so forth are implementing treatment on a trial basis throughout the world, existing combinations have to be discovered that have any noteworthy effects. Although Shosaikoto has been reported to be effective in vitro, definite efficacy in human beings has yet to be reported. Thus, it is necessary to not confine studies to use of the present knowledge of oriental medicine, but rather seek out a herb medicine found throughout nature that is not routinely used, based on the introduction of a completely new concept.

A pharmaceutical of oriental medicine along the herb medicines that compose it are determined according to diagnosis using oriental medicine (herbal medicine) techniques. This diagnosis is unique to oriental medicine, and differs from that found in western medicine and other means of natural therapy. The composition is determined according to the disease state of the individual, can certainly not be determined according to the name of the illness.

However, since the AIDS treatment developed by the inventors of the present invention is to be effectively used throughout the world, including the U.S. and Europe where oriental medicine has not fully progressed, a composition must be applicable to nearly all AIDS patients.

Based on the manner of thinking described above, the inventors of the present invention minutely searched through a total of 1500 types of oriental drugs used in oriental medicine, including roughly 600 types of non-routine new herb medicines, as well as roughly 1500 types of herb medicines used in traditional medicine in South America, Europe, India, Indonesia and Africa based on their experience in the field of oriental medicine, over the past roughly 8 years starting several years after AIDS was reported. A new composition was recently discovered that consists entirely of a herb medicine, has hardly any adverse side effects and can be taken easily. This new composition was actually used in 110 cases over the course of two years. As a result, this new composition was confirmed to have excellent efficacy making it remarkably beneficial as a treatment for AIDS, thus leading to completion of the present invention.

In the preparing of a composition effective against AIDS, it is necessary to select ingredients from those having effects shown below in consideration of the AIDS disease state, its causes and various related conditions. Namely, those effects considered to be required can be divided into three types of actions consisting of: (1) anti-inflammatory, anti-fever, expectorant or anti-tussive action, (2) nourishment, tonic, good for the gastrointestinal tract or digestive action, and (3) anti-fungal or anti-viral action.

The following factors must be taken into consideration in the selection of herb medicines having these actions.

(a) Composition is typically blended based on a proportion of several types of herb medicines. These compositions demonstrate clinical effectiveness in the form of the total effectiveness of the particular ingredients. Namely, rather than the total sum of each of the effects of each herb medicine, these compositions are used by taking advantage of the synergistic and conflicting actions of each herb medicine used. Thus, instead of selecting herb medicines for the individual actions that are demonstrated by each, they must be selected while taking into consideration the overall blend of the herb medicine that respectively demonstrates the three types of actions listed above.

(b) Since AIDS is a disease unlike any disease that has appeared in the history of mankind, it cannot be said to be completely handled even with Chinese medicine (oriental medicine) based on experience accumulated over the course of 3000 years. Thus, in addition to the herb medicines that have been described thus far, a wide range of herb medicine ingredients must also be sought out, such as folk medicines and the numerous plants found in the wild.

(c) Herb medicine ingredients must not exhibit toxicity to the human body. In addition, these ingredients must be selected so that they can be taken easily by patients having debilitated physical strength and appetites by giving consideration to the taste and aroma when taking the medicine.

(d) Although AIDS is an infectious disease, it progresses in chronic fashion in the same manner as tuberculosis. Thus, it is desirable to select herb medicine ingredients that are, suitable for taking for an extended period of time, namely those that do not have toxicity or adverse side effects when used in the past in a large number of cases over a long period of time.

(e) Since the disease is frequently complicated with gastrointestinal disorders and anorexia in the majority of patients, it is preferable that only a small number of types of herb medicine ingredients be required to be taken, and moreover, that they only be required to be taken in small amounts. This is also preferable in economic terms as well. Thus, it is more preferable that a single herb medicine have not only anti-inflammatory and anti-fever action, but also the effective actions described above.

Based on the above viewpoints, the following herb medicines were selected having the actions indicated below.

(1) Anti-inflammatory, Anti-fever, Expectorant and Anti-tussive Action

*Melia azedarach* L., *Angerica dahurica* B & H., *Dendrobium hancockii* R., *Impatiens balsamina* L., *Citrus medica* L., *Loranthus parasiticus* Merr., seeds of *Gelosia angentea* L., roots of *Cynanchum glaucescens* (Decne.) Hand. Mazz., and *Glehnia littoralis* Fr.

(2) Nourishment, Tonic, Gastrointestinal Tract Function Improving, Digestive Action

*Prunus amygdalus* Batsch., *Dioscorea batatas* Decne., *Dendrobium hancockii* R., *Loranthus parasiticus* Merr.,

*Paullinia cupana* Kunth, *Acer saccarum* Marsh., *Citrus medica* L., and *Glycyrrhiza glabra* L.

(3) Anti-fungal and Anti-viral Action

*Glehnia littoralis* Fr., *Angerica dahurica* B & H, *Loranthus parasiticus* Merr., *Impatiens balsamina* L., and *Gloiopeltis tenax* T.A.

A weight ratio of herb medicins representing the groups (1) to (3) is preferably the group (1) 9~3: group (2) 9~3: group (3) 6~1. In another embodiment, a weight ratio of herbmedicins representing the groups (1) to (3) is preferably the group (1) 3: group (2) 1~3: group (3) 0.5~2.

Each of the above-mentioned herb medicines contain the following components and demonstrate the following actions.

*Melia azedarach* L.

Components: tannin, toosendanin etc.

Actions: anti-parasitic effect, anti-inflammatory effect

*Angepica dahurica* B & H

Components: angellicin, angelicol etc.

Actions: anti-biotic effect, pain killer effect, anti-viral effect, detoxication

*Denclrobium hancockii* R.

Component: dendrobine etc.

Actions: tonic effect (especially for lung disease), anti-fever effect, pain killer effect, good for gastrointestinal tract, anti-inflmmnatory effect

*Impatiens balsamina* L.

Components: kaempferol, quercetin, etc.

Actions: anti-inflammatory action, anti-biotic and anti-viral actions, detoxication, anti-tumor effect

*Citrus medica* L.

Components: hesperidin, essential oil etc.

Actions: good for gastrointestinal tract, anti-tussive and sputum expectorant effect etc.

*Loranthus parasiticus* Merr.

Components: avicularin, quercetin

Actions: heart stimulant effect, anti-biotic effect, anti-viral effect, diuretic effect Seeds of *Celosia angentea* L.

Components: fatty oil

Actions: anti-biotic effect, anti-hypertension effect

Roots of *Cynanchum glaucescens* (Decne.) Hand. Mazz.

Component: saponin

Actions: anti-tussive and sputum broncho-ectasic action

*Glehnia littoralis* Fr.

Components: saponin, inulin

Actions: anti-fungal effect, tonic effect, anti-tussive and sputum expectorant effect

*Prunus amygdalus* Batsch

Components: amygdarin, emulsin, vitamins

Actions: anti-tussive and sputum expectorant action, lenitive action

*Dioscorea batatas* Decne.

Components: saponin, arginin, amylase

Actions: digestive effect, tonic effect, anti-DM effect, nourishment

*Paullinia cupana* Kunth

Components: caffeine, saponin

Actions: tonic effect, anti-diarrhea effect, anti-headache effect

*Acer saccarum* Marsh,

Component: glucose

Action: sweetening effect

*Glycyrrhiza glabra* L.

Component: glycyrrhizin

Actions: anti-inflammatory effect, steroid hormone-like effect, anti-allergic effect, anti-gastric ulcer effect, detoxication effect

*Gloiopeltis tenax* T.A.

Actions: anti-vital effect (influenza virus), malaise resolving effect

The pharmaceutical composition of the present invention is blended by selecting at least one type of herb medicine from the groups of herb medicines having each of the actions described above. However, in the case a single herb medicine belongs to two or more groups, when a certain herb medicine is selected from one group, another herb medicine must be selected from another group. Thus, the pharmaceutical composition of the present invention must always contain at least 3 more types of herb medicines.

In the present invention, the types of herb medicines used and their blending ratios are determined according to the condition of the AIDS patient. For example, in winter, a composition is preferable that contains mainly (1) a herb medicine having anti-inflammatory, anti-fever, expectorant and anti-tussive action, and (2) a herb medicine that has anti-viral action for influenza, cold and following bronchitis and pneumonia that occur easily in AIDS patients. This type of composition preferably contains *Angerica dahurica* B & H, *Dendrobium hancockii* R., roots of *Cynanchum glaucescens* (Decne) Hand Mazz., *Dioscorea batatas* Decne., *Melia azedarach* L., *Loranthus parasiticus* Merr., *Glycyrrhiza glabra* L., *Acer saccarum* Marsh and *Gloiopeltis tenax* T.A. The preferable ratios of this composition are 3 parts by weight of *Dioscorea batatas* Decne. and *Melia azedarach* L., 2 parts by weight of *Loranthus parasiticus* Merr., *Angepica dahurica* B & H and *Dendrobium hancockii* R., and 1 part by weight of *Glycyrrhiza glabra* L., *Gloiopeltis tenax* T.A., *Acer saccarum* Marsh. and roots of *Cynanchum glaucescens* (Decne.) Hand. Mazz.

Alternatively, composition preferably comprises *Prunus amygdalus* Batsch., *Celosia argentea* L., roots of *Loranthus parasiticus* Merr., *Dioscorea batatas* Decne., *Melia azedarach* L., *Loranthus parasiticus* Merr., *Glycyrrhiza glabra* L., *Acer saccarum* Marsh., *Citrus medica* L. and *Paullinia cupana* Kunth.

Preferable ratio of these components is 3 parts by weight of *Dioscorea batatas* Decne., 3 parts by weight of *Melia azedarach* L., 2 parts by weight of *Loranthus parasiticus* Merr., 2 parts by weight of *Prunus amygdalus* Batsch., 2 parts by weight of *Celosia argentea* L, 1 part by weight of *Glycyrrhiza glabra* L., 1 part by weight of *Citrus medica* L., 1 part by weight of *Acer saccarum* Marsh., and 1 part by weight of *Paullinia cupana* Kunth.

In addition, in the case AIDS patients are complicated with fungal diseases, it is necessary to use *Glehnia littoralis* Fr. in a herb medicine having anti-fungal and anti-viral action. For example, *Dioscorea batatas* Decne., *Melia azedarach* L., *Angerica dahurica* B & H, *Loranthus parasiticus* Merr., roots of *Cynanchum glaucescens* (Decne.) Hand. Mazz., *Glycyrrhiza glabra* L., *Glehnia littoralis* Fr., *Citrus medica* L., and *Acer saccarum* Marsh are used, and their ratios are preferably 3 parts by weight of *Dioscorea batatas* Decne. and *Melia azedarach* L., 2 parts by weight of *Angerica dahurica* B & H, *Loranthus parasiticus* Morr. and roots of *Cynanchum glaucescens* (Decne.) Hand Mazz., and 1 part by weight of *Glycyrrhiza glabra* L., *Glehnia littoralis* Fr., *Citrus medica* L., and *Acer saccarum* Marsh.

Moreover, in the case AIDS patients have symptoms of gastroenteritis or chronic diarrhea, a composition is preferable that primarily contains a herb medicine that is good for the gastrointestinal tract and has digestive action. This type of composition contains, for example, *Dioscorea batatas* Decne., *Melia azedarach* L., *Dendrobium hancockii* R., *Loranthus parasiticus* Merr., *Angerica dahurica* B & H, *Glycyrrhiza glabra* L., *Citrus medica* L., *Cynanchum glaucescens* (Decne.) Hand. Mazz. (or *Paullinia cupana* Kunth), and *Acer saccarum* Marsh. The ratios of these are, for example, 3 parts by weight of *Dioscorea batatas* Decne. and *Melia azedarach* L., 2 parts by weight of *Dendrobium hancockii* R., *Loranthus parasiticus* Merr. and *Angerica dahurica* B & H, and 1 part by weight of *Glycyrrhiza glabra* L., *Citrus medica* L., *Cynanchum glaucescens* (Decne.) Hand. Mazz. (or *Paullinia cupana* Kunth), and *Acer saccarum* Marsh.

In the present invention, a composition containing at least *Melia azedarach* L., *Dioscorea batatas* Decne., *Loranthus parasiticus* Merr., *Angerica dahurica* B & H, *Dendrobium hancockii* R., *Paullinia cupana* Kunth, *Glycyrrhiza glabra* L. (or *Acer saccarum* Marsh.), and *Gloiopeltis tonax* T.A. (or *Citrus medica* L.) is typically preferable, and their ratios are, for example, 3–10 parts by weight of *Melia azedarach* L. and *Dioscorea batatas* Decne., 2–8 parts by weight of *Loranthus parasiticus* Merr., *Angepica dahurica* B & H and *Dendrobium hancockii* R., and 0.5–3 parts by weight of *Paullinia cupana* Kunth, *Glycyrrhiza glubra* L. (or *Acer saccarum* Marsh.) and *Gloiopeltis tonax* T.A. (or *Citrus medica* L.).

Normally, herb medicines are effective when taken either between meals or on an empty stomach. In special cases, such as cases when patients have gastrointestinal disorders or toxicity, they may be directed to be taken after meals. In the case of the pharmaceutical composition for treating AIDS of the present invention, herb medicines are selected in consideration of not causing gastrointestinal disorders. Moreover, since these herb medicines are believed to be completely free of toxicity, there have been no objective or subjective findings indicating toxicity observed based on actual experience.

The pharmaceutical composition for treating AIDS of the present invention is normally administered orally. In this case of administration to normal adults, all of the component herb medicines are blended at their prescribed ratios at a proportion of 4–12 g of the maxim weight of the component herb medicines, the herb medicines are brewed for roughly 30–50 minutes in a suitable amount (300–500 ml) of mineral water (natural water), the solution is brewed down to a total of roughly 200 ml, and then taken 2–3 times per day 20–30 minutes before meals. In the case of children, the amount is reduced corresponding to body weight. An amount equal to roughly ⅓ the amount for adults is suitable for children roughly 6 years old. In addition, when it is difficult to take the herb medicine due to its characteristic bitter taste, natural maple syrup and honey are allowed to be added as the best sweeteners. In addition, when administered in the form of an extract, a suitable amount of vehicle may be added to form granules or tablets, while the syrups or cookie-like compositions can be formed for administration to children. In addition, a powder of the raw herb medicine can be combined with maple syrup or honey to form into pills.

On the other hand, in the case oral administration is impossible for whatever reason, the composition of the present invention can also be administered by injection, suppository (enema), inhalation and so forth. For example, the composition can be administered in the form of subcutaneous injection, intramuscular injection, intravenous drip or intravenous injection by preparing an injection solution of herb medicine as is performed in modern Chinese oriental medicine. In addition, a suitable amount can be injected into the rectum or inhaled through the use of a nebulizer.

EXAMPLES

The following provides a detailed explanation by Examples. However, the scope of the present invention is by no means limited by the following embodiment.

Example 1

The composition, dose and dosing method of the pharmaceutical composition for treating AIDS of the present invention used in this Example are as shown below.

The body weights prior to treatment of 55 infant AIDS patients used in this Example were 7.7–14.3 kg (mean: 10.75 kg), for actual administration, the present composition, composed at the weight ratios of: 1.5 g of *Melia azedarach* L., 1.5 g of *Dioscorea batatus* Dence., 1.0 g of *Prunus amygdalus* Batsch., 1.0 g of *Dendorobium hancockii* R., 1.0 g of *Loranthus parasiticus* Merr., 0.5 g of *Glycyrrhiza glabra* L., 0.5 g of *Citrus medica* L., 0.5 g of *Paullinia cupana* Kunth. and 0.5 g of *Acer saccarum*. Marsh. with respect to a body weight of 10 kg, was placed in roughly 100 ml of mineral water, brewed down to 30 ml for roughly 40 minutes over a low flame, and administered orally twice a day (30 minutes before the morning and evening meals as a general rule).

The 55 patients were divided to 5 groups the test groups were as follow: The 55 patients were divided to 5 groups the test groups were as follow:

Group I: the present composition (9 patients)

Group II: the present composition+astol+soup (22 patients)

Group III: the present composition+astol+soup+AZT 6 mg/kg/day (8 patients)

Group IV: AZT (8 patients)

Group V: untreated control group (8 patients)

$CD_4$ cell count and $CD_4/CD_8$ rate were measured four times (before treatment, five months, seven months and a year after treatment). As seen from FIG. 1, $CD_4$ cell count of Groups I and II measured at significantly higher than the other groups. Groups III, and IV (treated with only AZT) and V (control) measured much lower, while suppprisingly, Group IV had the lowest $CD_4$ cell count. So, the present composition maintains the $CD_4$ of pediatric AIDS patients at a high level. We must consider the possibility that AZT has a side effect of depressing the lymphatic system in the human body, despite its direct effect on the HIV virus.

The clinical results were measured six months after treatment.

To decide the clinical effect the following clinical symptoms were observed:

Fever

Cough and sputum (chronic)

Lymphadenopathy

Weight loss

Chronic diarrhea

Appetite

Nausea (with vomiting)

Malaise (fatigue)

Night sweating

Skin disease

Stomatitis

Hepatomegally
Spenomegally
Neurological disorder

Each symptom was given +1 score if it became worse, and the definition of clinical condition were as follows:

Excellent: −4 - - -
Good: −2 - - - −3
Same (unchanged): +1 - - - −1
Worse: +2 - - -

Figure 2:
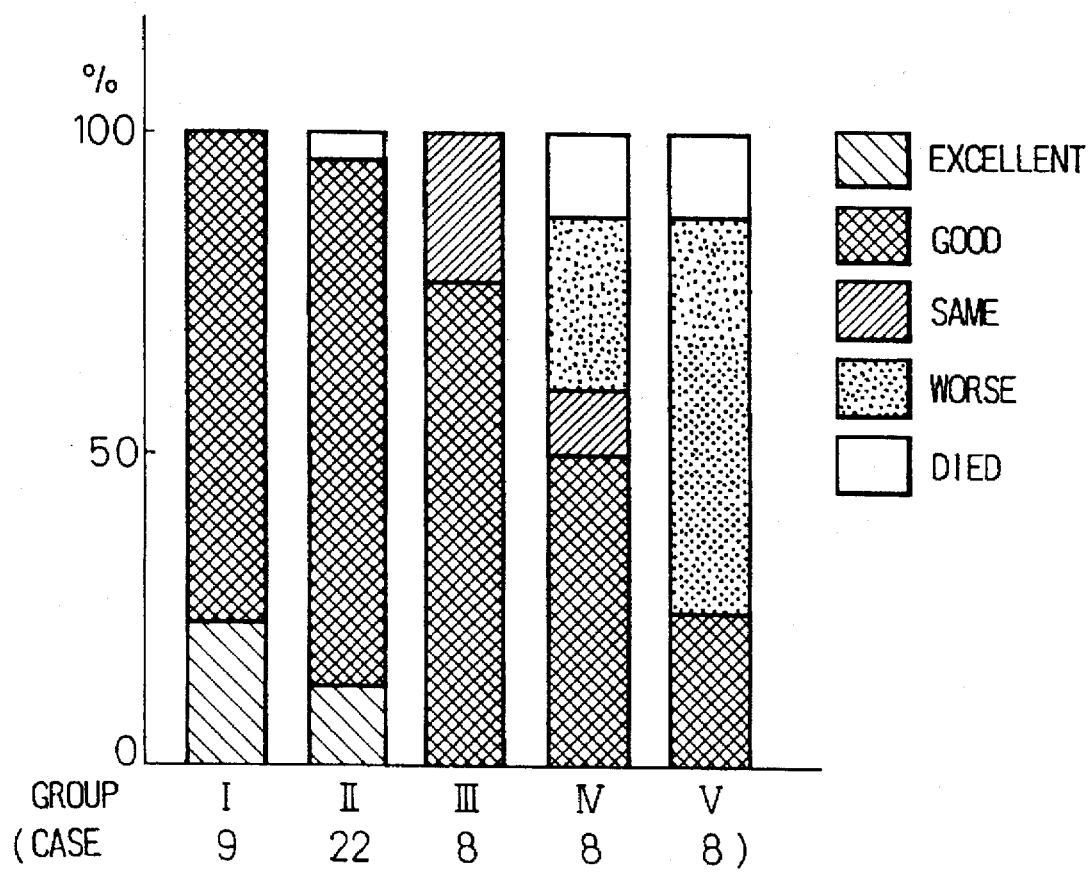
FIG. 2 is a graph showing clinical observation of each of the same group as in FIG. 1.

As seen from FIG. 2, the improvement is seen in Groups I, II and III, especially in Group I and II.

Figure 3:
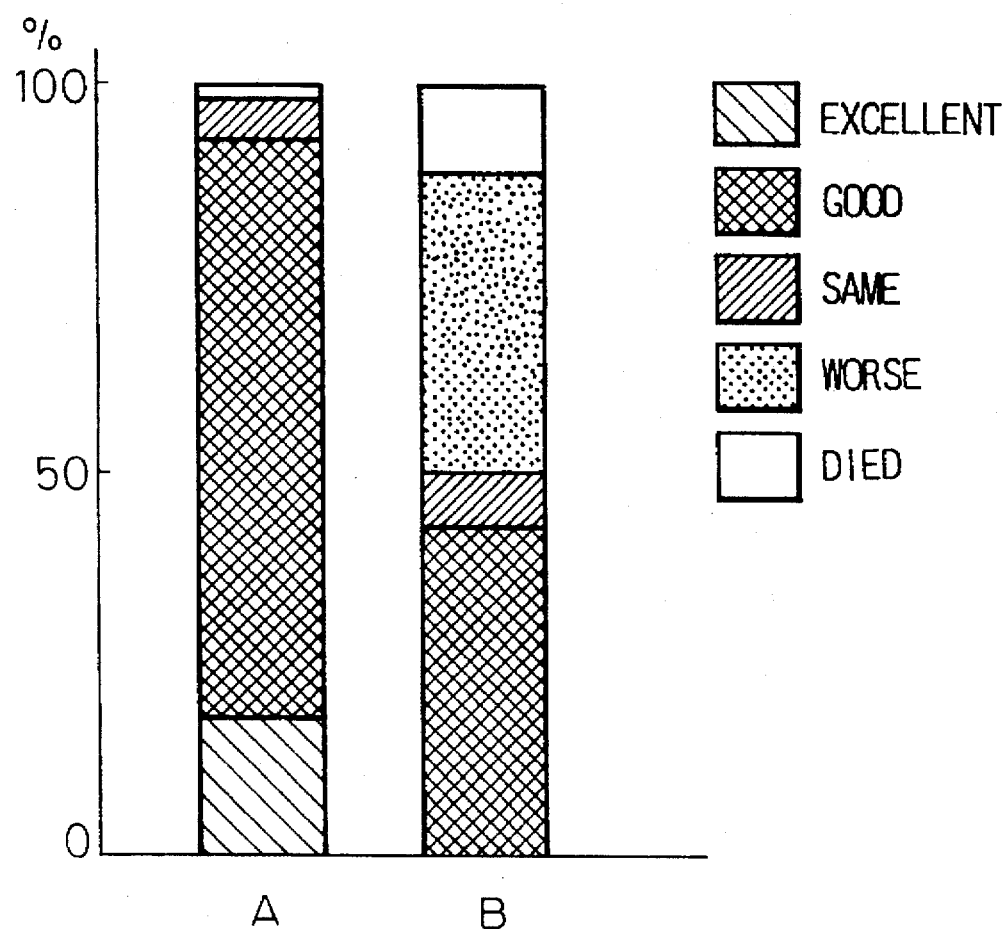
FIG. 3 is a graph comprising clinical observation of the group treated with the present composition or other medicines.

The clinical results (A) obtained from Groups I, II and III using the present composition and the clinical results (B) obtained from Groups IV and V not using the present composition are compared in FIG. 3. FIG. 3 clearly shows the clinical differences between the groups treated with the herbs and those not treated.

Example 2

The experiment as described in Example 1 was compared with other 211 patients. Among 31 patients treated with the present composition, one patient died in one year (notality 3.1%), while among 211 patients treated with conventional method not using the present composition, 48 patients died in one year (notality 22.7%), as shown in FIG. 4.

The present inventor have already treated about 110 pediatric AIDS patients and a few adults at two hospitals for 18 months.

Through these procedures, the patients did not experience any side effects or toxic symptoms, and almost all patients who have been treated with the present composition became much better clinically, and began to grow again both physically as well as mentally. Clinical recovery of adults was similar to the children, even in the few cases we observed.

The Advantages of this treatment:

a. The present medicine is made of only natural materials, consequently it has no toxins and no side effects at all as compared with chemical medicines.
b. This treatment is gentle enough for weak patients who have suffered from the HIV virus for a long time. It can also be used to treat patients of all ages and stages of illness.
c. This treatment keeps the $CD_4$ count level high, and therefore, protects the patient from the many secondary diseases or symptoms which accompany the HIV infection.
d. This treatment can be used with all other methods including chemical medicine (AZT, DDI, etc.), if the doctor or patient desires.
e. This treatment reduced the morality rate from 22.7% to 3.1%. 211 cases were treated without using the present composition, of which 48 cases were fatal. On the contrary, 31 cases were treated with the present composition and only one case died.

It is clear that this new treatment can prolong the patient's life safely and remarkably, also can prevent the complications caused by HIV infection, as it is well known that HIV virus does not kill human beings by itself.

In conclusion, the present invention has demonstrated that the present natural herbal treatment has a profound effect on the $CD_4$ count and consequently prolongs the life of the HIV positive patient.

I claim:

1. A pharmaceutical composition for treating acquired immune deficiency syndrome (AIDS) comprising:

(1) a herb medicine having anti-inflammatory, anti-fever, expectorant or antitussive action, selected from the group consisting of Melia azedarach L., Angepica dahurica B & H., Dendrobium hancockii R., Impatiens balsamina L., Citrus medica L., Loranthus parasiticus Merr., seeds of Celosia argentea L., roots of Cynanchum glaucescens (Decne.) Hand. Mazz., and Glehnia littoralis Fr.;

(2) a herb medicine having a nourishment, tonic, good for gastrointestinal tract or digestive action, selected from the group consisting of Prunus amygdalus Batsch., Dioscorea batatas Decne., Dendrobium hancockii R., Loranthus parasiticus Merr., Paullinia cupana Kunth, Acer saccarum Marsh., Citrus medica L., and Glycyrrhiza glabra L.; and (3) a herb medicine having an antifungal or anti-viral action, selected from the group consisting of Glehnia littoralis Fr., Angepica dahurica B & H., Loranthus parasiticus Merr., Impatiens balsamina L., and Gloiopeltis tenax T.A.;

with the proviso that when a herb medicine selected from one group also belongs to one or more other groups, another herb medicine must be selected from the other group so that the pharmaceutical composition comprises at least three herb medicines.

2. A pharmaceutical composition according to claim 1, which comprises 9 to 3 parts by weight of a medicine belonging to group (1), 9 to 3 parts by weight of a medicine belonging to group (2) and 6 to 1 parts by weight of a medicine belonging to group (3).

3. A method of treating a patient with AIDS to retard the progressive onset of the symptoms of AIDS which comprises administering to said patient the composition of claim 1.

4. A pharmaceutical composition for treating a patient with AIDS comprising Prunus amygdalus Batsch., Celosia argentea L., roots of Loranthus parasiticus Merr., Dioscorea batatas Decne., Melia azedarach L., Loranthus parasiticus Merr., Glycyrrhiza glabra L., Acer saccarum Marsh. Citrus medica L., and Paullinia cupana Kunth.

5. A pharmaceutical composition according to claim 4, comprising 3 parts by weight of Dioscorea batatas Decne., 3 parts by weight of Melia azedarach L., 2 parts by weight of Loranthus parasiticus Merr., 2 parts by weight of Prunus amygdalus Batsh., 2 parts by weight of Celosia argentea L., 1 part by weight of Glycyrrhiza glabra L., 1 part by weight of Citrus medica L., 1 part by weight of Acer saccarum Marsh., and 1 part by weight of Paullinia cupana Kunth.

6. A pharmaceutical composition for treating a patient with AIDS comprising Dioscorea batatas Decne., Melia azedarach L., Angepica dahurica B & H, Loranthus parasiticus Merr., roots of Cynanchum glaucescens (Decne) Hand Hazz., Glycyrrhiza glabra L., Glehnia littoralis Fr., Citrus medica L., and Acer saccarum Marsh.

7. A pharmaceutical composition according to claim 6, comprising 3 parts by weight of Dioscorea batatas Decne., 3 parts by weight of Melia azedarach L., 2 parts by weight of Angepica dahurica B & H, 2 parts by weight of Loranthus parasiticus Merr. 2 parts by weight of roots of Cynanchum glaucescens (Decne.) Hand Mazz., and 1 part by weight of Glycyrrhiza glabra L., 1 parts by weight of Glehnia littoralis Fr., 1 past by weight of Citrus medica L., and 1 part by weight of Acer saccarum Marsh.

8. A pharmaceutical composition for treating AIDS, comprising Dioscorea batatas Decne., Melia azedarach L., Dendrobium hancockii R., Loranthus parasiticus Merr., Angepica dahurica B & H, Glycyrrhiza glabra L., Citrus

*medica* L., *Cynanchum glaucescens* (Decne.) Hand. Mazz and *Acer saccarum* Marsh.

9. A pharmaceutical composition according to claim 8, comprising 3 parts by weight of *Dioscorea batatas* Decne., 3 parts by weights of *Melia azedarach* L., 2 parts by weight of *Dendrobium hancockii* R., 2 parts by weight of *Loranthus parasiticus* Morr. 2 parts by weight of *Angepica bahurica* B & H, 1 part by weight of *Glycyrrhiza glabra* L., 1 parts by weight of *Citrus medica* L., 1 part by weight of *Cynanchum glaucescens* (Decne.) Hand. Mazz, and 1 part by weight of *Acer saccarum* Marsh.

10. A pharmaceutical composition for treating a patient with AIDS, comprising *Melia azedarach* L., *Dioscorea batatas* Decne., *Loranthus parasiticus* Merr., *Angepica dahurica* B & H, *Dendrobium hancockii* R., *Cynanchum glaucescens* (Decne.) Hand. Mazz., *Glycyrrhiza glabra* L. or *Acer saccarum* Marsh., and *Gloiopeltis tanax* T.A.

11. A pharmaceutical composition according to claim 10, comprising 3–10 parts by weight of *Melia azedarach* L. 3–10 parts by weight of *Dioscorea batatas* Decne., 2–8 parts by weight of *Loranthus parasiticus* Merr., 2–8 parts by weight of *Angepica dahurica* B & H, 2–8 parts by weight of *Dendrobium hancockii* R., 0.5–3 parts by weight of *Cynanchum glaucescens* (Decne.) Hand. Mazz., 0.5–3 parts by weight of *Glycyrriza glabra* L. or *Acer saccarum* Marsh., and 0.5–3 parts by weight of *Gloiopeltis tonax* T.A.

* * * * *